United States Patent
Kushibiki et al.

[11] Patent Number: 5,116,369
[45] Date of Patent: May 26, 1992

[54] COMPOSITION FOR INTRAOCULAR LENS

[75] Inventors: Nobuo Kushibiki, Yamato; Noriyuki Nose, Machida; Yukichi Niwa, Narashino; Norio Kaneko, Atsugi, all of Japan

[73] Assignee: Canon Kabushiki Kaisha, Tokyo, Japan

[21] Appl. No.: 582,117

[22] Filed: Sep. 14, 1990

Related U.S. Application Data

[63] Continuation of Ser. No. 405,584, Sep. 11, 1989, abandoned, which is a continuation of Ser. No. 164,415, Mar. 4, 1988, abandoned.

[30] Foreign Application Priority Data

Mar. 6, 1987 [JP] Japan .................. 62-49907

[51] Int. Cl.$^5$ ................. A61F 2/14
[52] U.S. Cl. .................. 623/6; 351/160 H
[58] Field of Search .......... 351/160 H; 623/6

[56] References Cited

U.S. PATENT DOCUMENTS

| | | | |
|---|---|---|---|
| 4,537,943 | 8/1985 | Talcott | 528/15 |
| 4,542,542 | 9/1985 | Wright | 623/6 |
| 4,608,050 | 8/1986 | Wright | 623/6 |
| 4,647,282 | 3/1987 | Fedorov et al. | 623/4 |
| 4,698,386 | 10/1987 | Fujimoto | 524/862 |

FOREIGN PATENT DOCUMENTS 0204171 12/1986 European Pat. Off.
3532686 9/1985 Fed. Rep. of Germany.

Primary Examiner—David J. Isabella
Assistant Examiner—Debra S. Brittingham
Attorney, Agent, or Firm—Fitzpatrick, Cella, Harper & Scinto

[57] ABSTRACT

A composition for an intraocular lens comprising, an organopolysiloxane (A) having a viscosity of 10,000 cp or below and comprising at least one unsaturated aliphatic group, an organopolysiloxane (B) comprising at least three hydrogenated silyl units and a platinum compound; wherein the platinum compound based on its platinum content constitutes 10–200 ppm by weight of the composition. The composition provides a homogeneous intraocular lens even when it is injected into a crystalline capsule through a slender tube such as an injection needle.

11 Claims, 3 Drawing Sheets

F I G. 4
F I G. 5

COMPOSITION FOR INTRAOCULAR LENS

This application is a continuation of U.S. application Ser. No. 07/405,584 filed Sep. 11, 1989, now abandoned, which is a continuation of U.S. application Ser. No. 07/164,415 filed Mar. 4, 1988, now abandoned.

FIELD OF THE INVENTION AND RELATED ART

The present invention relates to a composition for an intraocular lens capable of providing a transparent elastomeric member used as an intraocular lens, i.e., a substitute or ersatz for a crystalline lens nucleus.

Hitherto, the treatment of cataract has been conducted by enucleating a clouded crystalline lens under a surgical operation and transplanting an artificial lens into the crystalline lens cavity thereby to recover the sight after the operation. Recently, the "in the bag" method, i.e., a method wherein such artificial lens is inserted into the crystalline capsule or capsula lentis, has been a leading method since this method has been considered to cause little complication disease involved in the transplantation.

In such artificial lenses, there are naturally no large differences in the shapes of their lens portion, but the shapes of a lens-supporting member called as "haptic" have mostly been improved and modified repeatedly. As the material for the artificial lens, polymethyl methacrylate has mainly been used. On the other hand, the material for the lens-supporting member, polymethyl methacrylate, polyvinylidene fluoride, etc., have been used. Further, there have recently been developed artificial lenses comprising a silicone resin or a hydrogel such as Hydron (Am. Hydron Corp.) since the size of incision for the operation may be reduced by using these materials.

However, all of these conventional artificial lenses have been shaped into a lens in advance and thereafter inserted into the crystalline capsule. Therefore, these artificial lenses have some problems including molding precision such as flash or fin often involved in molded products, and toxicity based on a residual disinfectant (e.g., ethylene oxide), a residual monomer, etc.

In addition to the above-mentioned method wherein an artificial lens shaped in advance is inserted into an incised crystalline capsule, there has been proposed a method wherein a cataractous lens nucleus is removed while preserving the crystalline capsule, and the resultant empty crystalline capsule is then refilled with a substitute for the lens nucleus. With respect to such method, for example, J-M. Parel et al. have proposed a surgery procedure wherein a silicone resin is injected into an animal crystalline capsule and then cured or hardened (Graefe's Archive Opthalmology) 224, 165-173 (1986)).

However, according to our study, in a case where the above-mentioned Parel's method is used, the curing velocity of the silicone resin injected into a crystalline capsule is extremely small and it is difficult to obtain an artificial lens excellent in transparency and homogeneity.

SUMMARY OF THE INVENTION

A principal object of the present invention is to solve the above-mentioned problems accompanying the prior art and to provide a composition for an intraocular lens capable of providing an intraocular lens having excellent characteristics when it is injected into a mold such as a crystalline capsule through a slender tube.

As a result of our study, it has been found that when a polysiloxane is injected into a crystalline capsule through a slender tube under pressure in the prior art, the polysiloxane molecules oriented or aligned in the direction of flow cause inhomogeneity or irregularity in the polysiloxane whereby an intraocular lens excellent in transparency and homogeneity cannot be obtained.

The composition for an intraocular lens according to the present invention is based on such discovery and comprises: an organopolysiloxane (A) having a viscosity of 10,000 cp or below at normal temperature and comprising at least one unsaturated aliphatic group in an average polymer molecule, an organopolysiloxane (B) comprising at least three hydrogenated silyl units in an average polymer molecule, and a platinum compound; wherein the platinum compound based on its platinum content constitutes 10-200 ppm by weight of the composition.

Incidentally, according to our knowledge, a composition for an intraocular lens (i.e., a material for the lens before curing) which provides a desirable intraocular lens (substitute for a lens nucleus) when injected into a crystalline capsule may particularly preferably satisfy the following requirements.

(1) Room-Temperature Curing Type

When the temperature of a human body is assumed to be 35°-37° C., the above-mentioned composition may preferably be one capable of being cured in a relatively short period of time at such temperature. The reason for this is that it is naturally impossible to considerably elevate the temperature of the composition which has been injected into the human body. Further, when a composition capable of being cured in a long period of time is used, a serious problem such as the leakage of the injected fluid can be caused.

(2) Addition-Type Curing Reaction

With respect to this viewpoint, in the above-mentioned Parel's method, there has been used a condensation-type silicone resin capable of being cured by the following reaction.

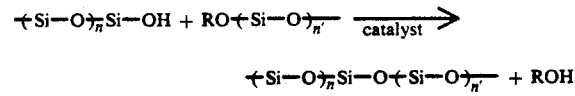

In the above reaction an alcohol (ROH) is necessarily eliminated, and this ROH generally comprises methanol. Because the ROH is incompatible with the polysiloxane, it is phase-separated and aggregates thereby to cause light scattering. Further, a catalyst such as dibutyltin laurate is generally used in the reaction as mentioned above. This type of reaction, however, has a small reaction velocity and it takes a period of one to several days to complete the reaction. Moreover, because the above-mentioned catalyst has a low solubility in the silicone resin produced by the curing reaction, it is generally difficult to obtain a silicone resin excellent in transparency.

On the contrary, the above-mentioned composition for an intraocular lens according to the present invention can retain a relatively low viscosity for a certain long period of time before curing (i.e., immediately after the composition is prepared by mixing the respective components), on the basis of the characteristic of a hydrosilylation reaction of an unsaturated aliphatic group such as a vinyl group with a hydrogenated silyl group. Further, the composition of the present invention, after being injected into a crystalline capsule through a slender tube may rapidly be cured or hardened by the hydrosilylation as an addition-type reaction without yielding a by-product.

Therefore, the composition for an intraocular lens according to the present invention, even when injected into a crystalline capsule through a slender tube such as an injection needle, does not cause inhomogeneity or irregularity based on the above-mentioned molecular chain orientation, and provides a homogeneous and transparent intraocular lens free of a decrease in transparency caused by a by-product etc., in the curing reaction.

These and other objects, features and advantages of the present invention will become more apparent upon a consideration of the following description of the preferred embodiments of the present invention taken in conjunction with the accompanying drawings. In the description appearing hereinafter, "part(s)" and "%" used for describing quantities are by weight unless otherwise noted specifically.

BRIEF DESCRIPTION OF THE DRAWINGS

FIGS. 4 and 5 are photographs by means of a zygo interferometer, respectively showing the homogeneity in the lenses obtained by using the compositions of Comparative Examples 1 and 2.

DETAILED DESCRIPTION OF THE INVENTION

Figure 1:
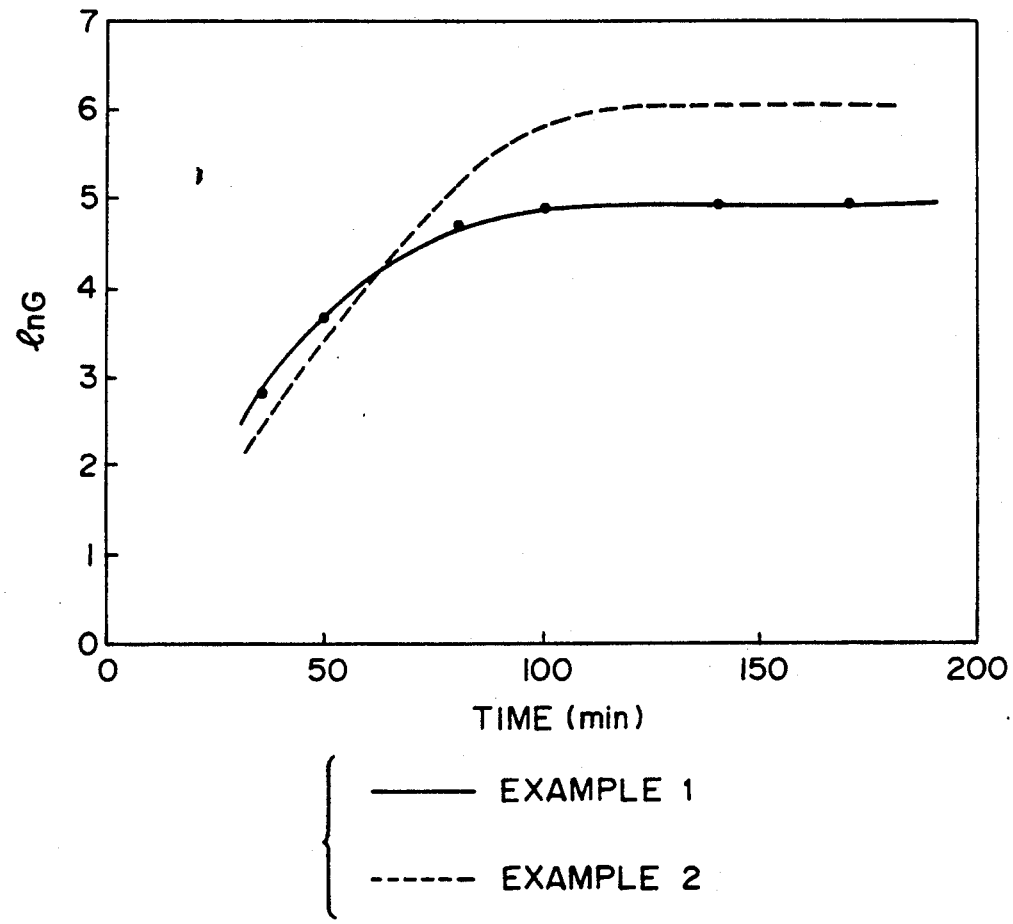
FIG. 1 is a graph showing a change in shear modulus in the compositions of the present invention obtained in Examples 1 and 2 described hereinafter, with the lapse of time.

The composition for an intraocular lens according to the present invention comprises an organopolysiloxane (A) comprising at least one unsaturated aliphatic group in an average polymer molecule thereof, an organopolysiloxane (B) comprising at least three hydrogenated silyl units in an average polymer molecule thereof, and a platinum compound as a curing catalyst. The organopolysiloxane used herein refers to an organic siloxane polymer comprising recurring units of siloxane

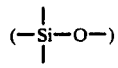

The above-mentioned organopolysiloxane (A) comprises at least one unsaturated aliphatic group in an average polymer molecule thereof, and may preferably comprise 1–5 unsaturated aliphatic groups. The unsaturated aliphatic group may be contained either in an intermediate unit in the polysiloxane chain, or in a terminal unit thereof. As the unsaturated aliphatic group, a 1-olefinic group such as vinyl, allyl, or 1-butenyl group may preferably be used.

The number or position of the unsaturated aliphatic group in the polysiloxane (A) may for example be confirmed by using an instrumental analysis such as nuclear magnetic resonance (NMR), more specifically, e.g., by using the area ratio between NMR peaks or the length of a relaxation time in NMR.

The polysiloxane (A) generally has a viscosity of 10,000 centipoises (cp) or below, preferably about 20–5,000 cp, more preferably about 20–2,000 cp at normal temperature (22° C., the same as in the description appearing hereinafter). Incidentally, the viscosity of the polysiloxane (A), polysiloxane (B) or a mixture thereof used in the present invention is that measured by means of a Couette-type rotary viscometer, Mechanical Spectrometer RMS-700, (mfd. by Rheometrics Corp.).

The molecular weight of the polysiloxane (A) corresponding to the above-mentioned viscosity may preferably be 60,000 or below, more preferably about 2,000–50,000, particularly preferably about 2,000–35,000. Particularly, in a case where the polysiloxane (A) is a copolymer-type comprising diphenylsiloxane, the polysiloxane (A) may preferably have a further low viscosity (e.g., 5,000 cp or below), since the degassing after mixing and stirring thereof generally takes a relatively long period of time.

The polysiloxane (A) used in the present invention can be obtained by using an ordinary process, and may for example be obtained by hydrolyzing a mixture of methylchlorosilane and vinylchlorosilane.

Specific examples of polysiloxane (A) used in the present invention may include those represented by the following formulas:

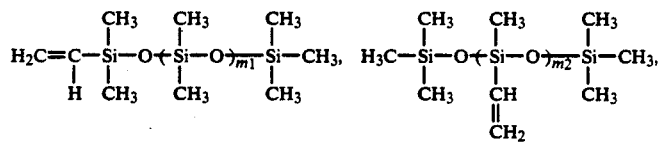

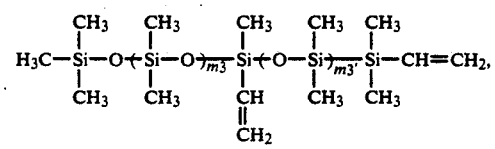

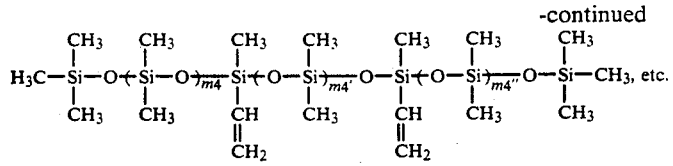

On the other hand, the polysiloxane (B) used for crosslinking the above-mentioned polysiloxane (A) comprises at least three hydrogenated silyl units

in an average polymer molecule thereof, and may preferably comprise 3-5 hydrogenated silyl units. The hydrogenated silyl unit may be either an intermediate unit in the polysiloxane chain, or a terminal unit thereof. If the polysiloxane (B) contains hydrogenate silyl units of below three, it is difficult to obtain a shear modulus suitable for an intraocular lens. On the other hand, if the polysiloxane (B) contains hydrogenated silyl units of above 5, an unreacted —SiH group is liable to be produced whereby such a residual active hydrogen tends to invite the deterioration of the polysiloxane.

The number or position of such hydrogenated silyl unit in the polysiloxane (B) may for example be confirmed by using an instrumental analysis such as nuclear magnetic resonance (NMR) in the same manner as described above.

The polysiloxane (B) preferably has a viscosity of 10,000 centipoises (cp) or below, more preferably about 20-5,000 cp, particularly preferably about 20-2,000 cp, at normal temperature (22° C.).

The molecular weight of the polysiloxane (B) corresponding to the above-mentioned viscosity may preferably be 60,000 or below, more preferably about 2,000-50,000, particularly preferably about 2,000-35,000.

The polysiloxane (B) used in the present invention can be obtained by using an ordinary process, and may for example be obtained by ring-opening-polymerizing a siloxane tetramer

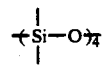

in the presence of a silane (or silicon hydroxide) compound comprising a hydrogenated silyl unit

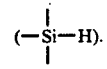

Specific examples of polysiloxane (B) used in the present invention may include those represented by the following formulas:

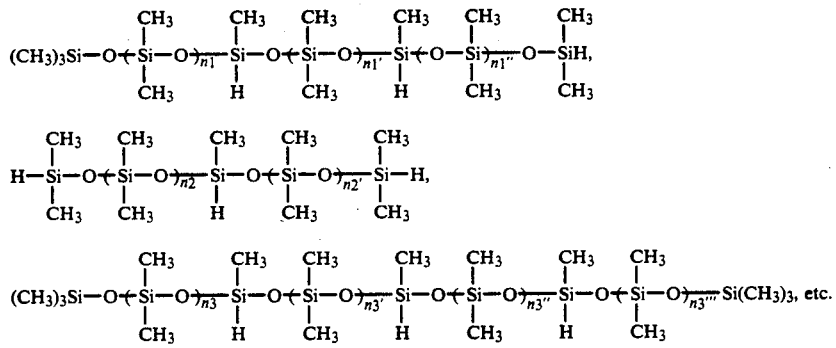

In the polysiloxane composition comprising the above-mentioned polysiloxanes (A) and (B) according to the present invention, these polysiloxanes may preferably be mixed so that the mole of the unsaturated aliphatic group in the polysiloxane (A) may be substantially equal to the mole of the hydrogenated silyl group in the polysiloxane (B). Therefore, while it is difficult to specifically determine the mixing ratio between these polysiloxanes, it is generally undesirable that either one of the unsaturated aliphatic group and the hydrogenated silyl group is present in excess in the resultant mixture of the polysiloxanes (A) and (B). More specifically, the polysiloxanes (A) and (B) may preferably be mixed so that the mole proportion may be about 0.9-1.1, more preferably about 0.9-1.0 in terms of a proportion of (mole of the hydrogenated silyl group)/(mole of the unsaturated aliphatic group).

Incidentally, the polysiloxane (A) or the polysiloxane (B) is not necessarily used as a single species but may be a mixture of different species of polysiloxane (A) or polysiloxane (B).

Further, the polysiloxane composition according to the present invention may preferably have a viscosity of 20-10,000 cp, more preferably 20-5,000 cp, particularly preferably 20-2,000 cp at normal temperature, in terms of the viscosity measured in a state where the composition is substantially unreacted or does not contain a platinum compound.

If the above-mentioned polysiloxane composition has a viscosity of above 10,000 cp, the composition is required to be injected into a crystalline capsule under a certain pressure when it is injected through a slender tube, e.g., an injection needle having an outside diameter of about 0.9 mm. In this case, the polysiloxane molecules may be oriented in the direction of flow and cause inhomogeneity or irregularity in the polysiloxane which has been injected into the crystalline capsule, whereby there can be formed only a lens which is optically distorted and is lacking in homogeneity. Incidentally, in such case, the viscosity can generally be decreased by elevating the fluid temperature, but such method cannot be used in the case of a reactive substance inclusive of the composition of the present invention.

In the polysiloxane composition of the present invention, it is preferred to use polysiloxane (A) comprising an unsaturated aliphatic group in a terminal unit of the polymer chain, in combination with a polysiloxane (B) comprising at least one hydrogenated silyl group (—Si—H) as an intermediate unit of the polymer chain. On the other hand, it is preferred to use a polysiloxane (A) comprising an unsaturated aliphatic group in an intermediate unit of the polymer chain, in combination with a polysiloxane (B) comprising at least one hydrogenated silyl group as a terminal unit of the polymer chain. In a case where the polysiloxanes (A) and (B) are combined in this manner, a cured or hardened product (i.e., an elastomeric member) having a desired shear modulus may easily be obtained by appropriately controlling the degree of crosslinking (or a network structure) in the curing reaction of the composition according to the present invention.

Further, characteristics of the above-mentioned polysiloxane (A) or (B) may be changed by modifying the siloxane structure as described hereinbelow.

Generally speaking, the refractive index of a polysiloxane can be increased by introducing a phenyl group, a halogen group, etc., thereinto. However, when a phenyl group is introduced into a polysiloxane at a high concentration, such polysiloxane is liable to crystallize. Even if a phenyl group is introduced at a low concentration, the refractive index is sometimes disturbed due to double refraction or irregularity in the concentration of the introduced phenyl group. It is supposed that such disturbance is caused by an orientation of molecules, e.g., based on Van der Waals force produced between the cyclic structures of a phenyl group, or caused by the fluidity of the polymer.

Further, in a case where a phenyl group is introduced by copolymerizing a phenyl-substituted siloxane such as diphenylsiloxane, and an alkyl-substituted siloxane such as dimethylsiloxane, the alkyl-substituted siloxane molecules, which has a greater reactivity than the phenyl-substituted siloxane, molecules, are liable to form a chain of themselves thereby to form a block or segment. Therefore, if the amount of the phenyl-substituted siloxane is too large, uniformity in refractive index or double refraction may deteriorate.

Accordingly, in a case where a phenyl group is introduced into a polysiloxane, it is required to appropriately set the concentration thereof, or reaction conditions of introduction thereof. For example, it is desirable to set the amount of a phenyl group introduced into a polymer to 30–35 mol % in terms of the mole ratio of the phenyl group to the sum of the phenyl and alkyl groups, i.e., the ratio of (mole of the phenyl group)/(mole of the phenyl group mole of the alkyl group). Incidentally, in this case, a refractive index of about 1.55 may be obtained. Further, e.g., in a case where the refractive index of the polymer is changed from 1.4 to 1.5, the focal length may be changed in a proportion of about 25%. Therefore, the focal length may be changed by changing or modifying the polysiloxane.

In the polysiloxane composition of the present invention, the organic groups connected to Si atoms may preferably comprise methyl and phenyl groups. Further, the proportion of the phenyl group, i.e., (mole of $C_6H_5$)/(mole of $C_6H_5$+mole of $CH_3$), may preferably be 40 mole % or below, more preferably 35 mole % or below.

Then, there is described a platinum compound, as a curing catalyst constituting the composition of the present invention in combination with the above-mentioned polysiloxanes (A) and (B).

In the present invention, platinum per se can be used as the above-mentioned platinum compound, but a platinum compound except platinum, or a platinic acid compound (i.e., platinic acid and its derivative) may preferably be used.

In view of a suitable velocity of the curing reaction, preferred examples of the platinum compound may include: a platinum coordination compound such as an olefin platinum complex and a phosphine platinum complex; and a chlorinated platinic acid compound such as tetrachloroplatinic acid. Further, there may more preferably be used a complex compound of a platinic acid compound with an unsaturated silicon compound such as a vinylsilane compound (monomer) as described hereinafter; or a platinum complex such as a vinylsiloxane platinum complex and a triphenylphosphine platinum complex.

Particularly preferred examples of the platinum compound may include the following compounds.

olefin platinum complex:

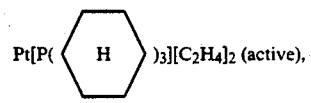

triphenylphosphine platinum complex:

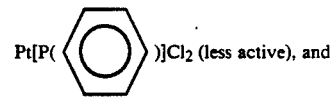

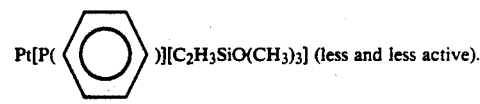

In the composition of the present invention, the amount of the platinum compound is 10–200 ppm, preferably 20–150 ppm, in terms of the weight of the platinum therein based on the total weight of the composition. If the amount of the platinum compound is below 10 ppm, the reaction velocity undesirably becomes too small. On the other hand, if the amount is above 200 ppm, not only the reaction velocity undesirably becomes too large but also platinum black is produced to cause light scattering.

When the platinum compound is contained in the composition of the present invention in an amount of 10–200 ppm, the composition may be cured for about 2–10 hours at a temperature of from room temperature to about 36° C. In this case, a hydrosilylation reaction represented by the following formula is caused, and a free substance (i.e., a by-product) is not produced in such curing.

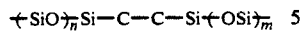

The polysiloxane composition of the present invention comprises the above-mentioned polysiloxane (A), the polysiloxane (B), and the platinum compound as a curing catalyst. The composition may further comprise an optional additive such as a retarding agent, as desired.

Specific examples of the retarding agent may preferably include unsaturated alcohols such as diacetylene alcohol; and unsaturated silicon compounds such as a vinylsilane compound (monomer).

The above-mentioned composition for an intraocular lens according to the present invention may preferably have a relatively low viscosity immediately after it has been prepared by mixing polysiloxanes (A) and (B), and a platinum compound (curing catalyst). On the other hand, the composition may preferably be cured rapidly to provide a lens after a prescribed time has passed from the preparation. In view of the convenience of handling (e.g., stability of the catalyst in storage) it is preferred that the curing catalyst is mixed in the polysiloxane (A) and the retarding agent, as desired, is mixed in the polysiloxane (B), while the present invention is not restricted to such combination. Further, the retarding agent may preferably be used in an amount which does not exceed that of the catalyst added to the composition, while the amount of the retarding agent may vary depending on the species thereof, or the reactivity or amount of the catalyst.

Generally, in the mixing of the polysiloxanes (A) and (B), the length of time required for measuring the amount, mixing and stirring them, and degassing the resultant mixture may be about 1-2 hours (or about 20-30 min. in a case where a particular vacuum mixing device is used). Therefore, in consideration of such time, the length of time for retarding the reaction may be determined. The length of time required from the initiation to completion of the curing may change depending on the above-mentioned mixing proportion in the composition or the rigidity of the product. Generally, the above-mentioned length of time of from the initiation to the completion may preferably be at most 6 hours, in a case where the time of completion is defined as the time at which the shear modulus (or modulus of rigidity) of the product reaches 95% of an intended shear modulus. Such shear modulus may be measured by means of a mechanical spectrometer RMS-700, (mfd. by Rheometrics Corp.).

The composition of the present invention may provide an intraocular lens by the curing reaction as described above. The shear modulus (G) of the lens (after the curing) may preferably be $1 \times 10^3 - 5 \times 10^6$ dyne/cm$^2$. Further, the lens may preferably have a transmittance of 50% or larger, more preferably 85% or larger, at least with respect to visible radiation of 400-700 nm.

The composition for an intraocular lens according to the present invention may be injected, e.g., through a slender tube, into a crystalline capsule from which the lens nucleus has been removed in advance, and then cured or hardened thereby to form an intraocular lens, as an artificial lens, having desirable characteristics.

Incidentally, in the accommodation or focal length regulation of a human eye, when a ciliary muscle is contracted and a Zinn's zonule is relaxed, the stress exerted on a crystalline lens is reduced and the thickness thereof increases due to its elasticity whereby the refracting power of the crystalline lens increases. On the other hand, when the ciliary muscle is elongated, the refracting power of the crystalline lens decreases, contrary to the above.

Accordingly, when a polysiloxane which has been formed by curing the composition according to the present invention and has a relatively small shear modulus, is used as an artificial crystalline lens, the accommodation function of the human eye can be utilized as such. Such accommodation function cannot have been preserved in the prior art.

As described hereinabove, according to the present invention, there is provided an organopolysiloxane composition comprising two specific species of polysiloxane compounds and a curing catalyst of a platinum compound in a specific concentration range.

The polysiloxane composition of the present invention, even when injected into a crystalline capsule through a slender tube, provides a homogeneous or uniform intraocular lens which is free of inhomogeneity or distortion due to the orientation of polymer molecules in the injection, and is also free of a problem such as leakage of the injection fluid.

Hereinbelow, the present invention will be explained in further detail with reference to specific examples.

EXAMPLE 1

2 wt. parts of the following vinylpolydimethylsiloxane (A) having a viscosity of 3,000 cp at 25° C., and 2 wt. parts of the following hydrogenated polydimethylsiloxane (B) having a viscosity of 300 cp at 25° C. were uniformly mixed to prepare a mixture.

(Polysiloxane (A))
number of siloxane recurring units: n=560,
number of vinylsilane units contained in a polymer molecule=3,

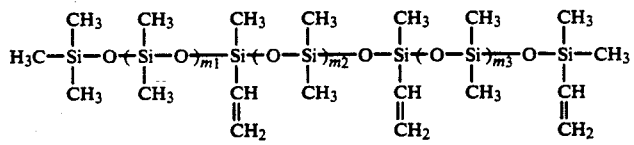

(Polysiloxane (B))
number of recurring units: n=190,
number of hydrogenated silyl units contained in a polymer molecule=3,

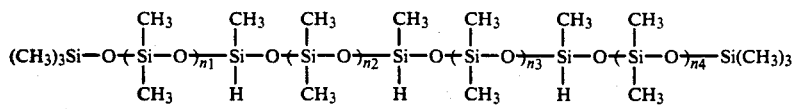

In the resultant mixture, a curing catalyst of a vinyltrimethoxysilane-platinic acid complex (a complex of 1 mole of platinic acid with 10 mole of vinyltrimethoxysilane) was mixed so that the weight of the platinum atoms was 100 ppm based on the total weight of the resultant composition, thereby to prepare a composition for an intraocular lens according to the present invention.

The composition prepared above was charged into a mold, which had a cavity having a diameter of 25 mm and a space of 3 mm, and comprised a hollow cylindrical wall of stainless steel and two circular glass plates, and left standing in an atmosphere of dry air at 30° C., thereby to cure the composition. In this case, the change in the curing degree was followed by means of a mechanical spectrometer RMS-700,(mfd. by Rheometrics Corp.), in terms of the change in a shear modulus G (dyne/cm$^2$). The results are shown in FIG. 1. As shown in FIG. 1, the composition of this instance was substantially completely cured about 100 min. after the preparation thereof.

Separately, 20 ml of above-mentioned composition of this instance was injected into a glass mold having a cavity which had the shape of a plano-convex lens, a space of 1 mm at the central portion, a spherical portion with a curvature radius of 53.7 mm and a bottom portion with a radius of 20 mm, at an injection rate of 1 ml/10 min. by using an injection needle having an outside diameter of 0.9 mm and a length of 50 mm. Then, the composition was left standing for 100 min. in an atmosphere of 30° C. to cure the composition whereby a plano-convex lens was formed.

Figure 2:
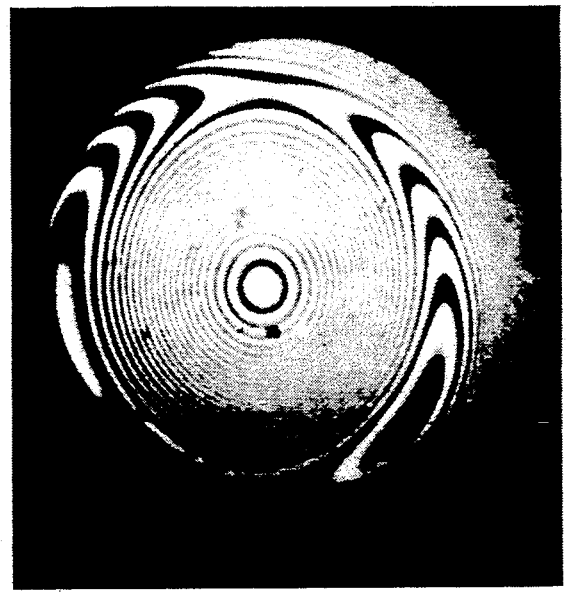
FIGS. 2 and 3 are photographs by means of a zygo interferometer, respectively showing the homogeneity in the lenses obtained by using the compositions of Examples 1 and 2.

The homogeneity in refractive index of the thus formed lens was measured by means of an interferometer using interference fringes of light (Interferometer Mark II, mfd. by Zygo Corporation, USA). The result is shown in the photograph of FIG. 2. As shown in FIG. 2, it was recognized that the composition of this instance had provided a lens excellent in homogeneity.

EXAMPLE 2

A composition for an intraocular lens was prepared in the same manner as in Example 1 except that the following polyvinylsiloxane copolymer was used as a polysiloxane (A), and the following hydrogenated polysiloxane copolymer was used as a polysiloxane (B), respectively.

(polysiloxane (A))

viscosity: 2,000 cp (25° C.), number of recurring units: n=480, number of vinylsilane units contained in a polymer molecule: 3, mole ratio of (diphenylsiloxane)/(dimethylsiloxane)=3/7.

(polysiloxane (B))

viscosity: 1,000 cp (25° C.), number of recurring units: n=360, number of hydrogenated silyl units contained in a polymer molecule: 3.

The curing reaction of the composition prepared above was followed in the same manner as in Example 1. The results are shown in a graph (dotted line) of FIG. 1.

Figure 3:

Further, a lens was formed in the same manner as in Example 1 except that the above-mentioned composition of this instance was used. The thus formed lens had a homogeneity in refractive index as shown in the photograph of FIG. 3 measured by means of the Zygo interferometer.

COMPARATIVE EXAMPLE 1

A composition for a lens was prepared in the same manner as in Example 1 except that a vinylpolysiloxane having a viscosity of 100,000 cp (n=1330) and containing two vinylsilane units in a polymer molecule was used as a polysiloxane (A). The thus prepared composition was injected into a mold for a lens by using an injection needle having the same outside diameter as that used in Example 1, and cured in the same manner as in Example 1 thereby to obtain a cured product.

FIG. 4 shows a photograph of the thus obtained cured product measured by means of the Zygo interferometer. As shown in FIG. 4, the cured product did not shown homogeneity nor optical characteristics as a lens.

COMPARATIVE EXAMPLE 2

A composition for a lens was prepared in the same manner as in Example 1 except that a vinylpolysiloxane having a viscosity of 20,000 cp at 25° C. (n=260) and containing two vinylsilane units in a polymer molecule was used as a polysiloxane (A). The thus prepared composition was injected into a mold for a lens and cured in the same manner as in Example 1 thereby to obtain a cured product.

FIG. 5 shows a photograph of the thus obtained cured product measured by means of the zygo interferometer. As shown in FIG. 5, the cured product showed optical characteristics of lens which had been improved as compared with those in FIG. 4 (Comparative Example 1), but were poor as compared with those in FIG. 2 (Example 1) or in FIG. 3 (Example 2).

What is claimed is:

1. An intraocular lens having a shear modulus of $1 \times 10^3 - 5 \times 10^6$ dyne/cm$^2$ and a transmittance of at least 50% with respect to visible radiation of 400-700 nm; said lens comprising a cured product of a composition consisting essentially of:
   (i) an organopolysiloxane (A) having a molecular weight less than or equal to 60,000, a viscosity of 10,000 cp or below at normal temperature and comprising at least one unsaturated aliphatic group in an average polymer molecule;
   (ii) an organopolysiloxane (B) comprising at least three hydrogenated silyl units in an average polymer molecule; and
   (iii) a platinum compound, wherein said platinum compound based on its platinum content constitutes 10-200 ppm by weight of said composition.

2. An intraocular lens according to claim 1, wherein said organopolysiloxane (A) comprises 1-5 unsaturated aliphatic groups in an average polymer molecule.

3. An intraocular lens according to claim 1, wherein said organopolysiloxane (A) has a viscosity of 20-5,000 cp at normal temperature.

4. An intraocular lens according to claim 1, wherein said organopolysiloxane (B) comprises 3-5 hydrogenated silyl units in an average polymer molecule.

5. An intraocular lens according to claim 1, wherein said organopolysiloxane (B) has a viscosity of 10,000 cp or below at normal temperature.

6. An intraocular lens according to claim 5, wherein said organopolysiloxane (B) has a viscosity of 20-5,000 cp at normal temperature.

7. An intraocular lens according to claim 1, which has a viscosity of 20-10,000 cp at normal temperature before curing.

8. An intraocular lens according to claim 7, which has a viscosity of 20-5,000 cp at normal temperature before curing.

9. An intraocular lens according to claim 1, wherein said platinum compound based on its platinum content constitutes 20-150 ppm by weight of said composition.

10. An intraocular lens according to claim 1, having a transmittance of at least 85% with respect to visible radiation of 400-700 nm.

11. An intraocular lens according to claim 1, containing a retarding agent.

* * * * *